United States Patent
Ortiz

(10) Patent No.: US 10,750,880 B1
(45) Date of Patent: Aug. 25, 2020

(54) ALERT SYSTEM FOR RAILS

(71) Applicant: Jeffrey Ortiz, Brooklyn, NY (US)

(72) Inventor: Jeffrey Ortiz, Brooklyn, NY (US)

(*) Notice: Subject to any disclaimer, the term of this patent is extended or adjusted under 35 U.S.C. 154(b) by 0 days.

(21) Appl. No.: 16/658,282

(22) Filed: Oct. 21, 2019

(51) Int. Cl.
| G08B 21/00 | (2006.01) |
| A47D 15/00 | (2006.01) |
| A47D 9/00 | (2006.01) |
| G01G 19/52 | (2006.01) |
| G08B 7/06 | (2006.01) |
| G08B 21/02 | (2006.01) |
| G08B 21/18 | (2006.01) |

(52) U.S. Cl.
CPC .......... *A47D 15/00* (2013.01); *A47D 9/00* (2013.01); *G01G 19/52* (2013.01); *G08B 7/06* (2013.01); *G08B 21/02* (2013.01); *G08B 21/182* (2013.01)

(58) Field of Classification Search
CPC ......... A47D 15/00; A47D 9/00; G01G 19/52; G08B 7/06; G08B 21/02; G08B 21/182
See application file for complete search history.

(56) References Cited

U.S. PATENT DOCUMENTS

| 4,951,032 | A | * | 8/1990 | Langsam | A47D 7/02 340/522 |
| 5,057,819 | A | * | 10/1991 | Valenti | A47D 15/001 340/539.1 |
| 6,737,982 | B2 | * | 5/2004 | Slomowitz | A47D 7/02 340/539.15 |
| 9,629,475 | B2 | * | 4/2017 | Veron | A47D 9/00 |
| 2005/0138730 | A1 | * | 6/2005 | Henry | A47G 9/02 5/482 |
| 2011/0043359 | A1 | * | 2/2011 | Toler | A61B 5/6892 340/539.15 |
| 2015/0288877 | A1 | * | 10/2015 | Glazer | H04N 5/2251 348/77 |
| 2017/0055724 | A1 | * | 3/2017 | Eldridge | G08B 21/22 |

* cited by examiner

*Primary Examiner* — Phung Nguyen
(74) *Attorney, Agent, or Firm* — Sanchelima & Associates, P.A.; Christian Sanchelima; Jesus Sanchelima

(57) ABSTRACT

An alert system for rails that includes a cover assembly, sensors and an alert assembly is disclosed. There is a need to momentarily leave a child unattended while they sleep, for example. The child may unexpectedly awaken and attempt to climb over the rails of their crib. This is a dangerous situation that is to be prevented. Hence, the alert system includes a cover assembly that may be mounted and secured on top of railings of all sorts, such as a bed, crib or gate. The sensors may be configured to detect weight thereon and upon detection of a predetermined weight threshold being surpassed may generate alerts through the alert assembly. The alerts occur in the form of lights, an audible alarm through speakers, or to a mobile device. Thereby allowing alerts to occur even when the guardian and child are not near one another.

10 Claims, 3 Drawing Sheets

ALERT SYSTEM FOR RAILS

BACKGROUND OF THE INVENTION

1. Field of the Invention

The present invention relates to an alert system for rails and, more particularly, to an alert system for rails that is capable of detecting an attempt to climb over a rail that creates alerts upon detection of the attempt.

2. Description of the Related Art

Several designs for alert systems for rails have been designed in the past. None of them, however, include rail pads having integral pressure sensors which activate an audible alert or sends a signal wirelessly to a portable electronic device. As a guardian of a child and particularly a young child it may to necessary to keep an eye on the child as much as possible. However, it becomes nearly impossible to provide constant monitoring with all the tasks of everyday life that must be completed. For example, when a child is sleeping the parents may temporarily go away to complete the laundry. The child may unexpectedly awaken while the parent is away with other household tasks or chores. Being that children are curious and always finding their way into trouble. That now unmonitored child that has awaken may attempt to get out of their crib by attempting to climb over the crib railing. This can be a dangerous situation as there is no one currently monitoring the child and their safety is compromised. The child may successfully climb the crib railing and fall from a significant height towards the ground and injure themselves in the form of broken bones, for example. Hence there is a need for a device that can detect when there is an attempt by a child, for example, to climb over the railing of their crib. The device can then alert the guardian of the child in a variety of ways in order to prevent injury or death of the child from climbing a railing of any sort. The present invention can be used by guardians or caretakers to increase the safety of a child.

Applicant believes that a related reference corresponds to U.S. Pat. No. 4,951,032 issued to Andrew S. Langsam for Crib Rail Safety Annunciator. It is a crib rail safety monitor which alerts a child's attendant to a potential injurious situation when a child is located within a crib and the crib side rail in the down or lowered position. It includes a flashing light which will first alert the attendant of the situation without awakening the child. If the crib rail is in a lowered position and the attendant is not in the vicinity, then an audible alarm is activated. The crib rail position indicator can be an ordinary magnetic reed switch, the mechanism to confirm the presence of a child with the crib can be a weight sensor and the attendant's presence can be performed by an ultrasonic motion detector or an infrared temperature sensor. There are also timers which give the attendant the chance to secure the crib rail in a raised position. However, it differs from the present invention because the Langsam reference is intended only for cribs and it is to detect a rail in a lowered position. The present invention can be used on railings of all sorts not just crib rails. The present invention detects of weight on a rail to indicate that a child is attempting to climb over a rail. Additionally, the present invention can alert in the form of lights, auditory alarm and further an alert sent to a wireless device.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide an alert system for rails that increases the safety of a person such a child.

It is another object of this invention to provide an alert system for rails that detects the presence of weight upon rails when a person is attempting to climb over the rails.

It is still another object of the present invention to provide an alert in the case that there is detection of an attempt to climb over a rail in the form of lights, audible alert and a wireless message to a mobile device.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
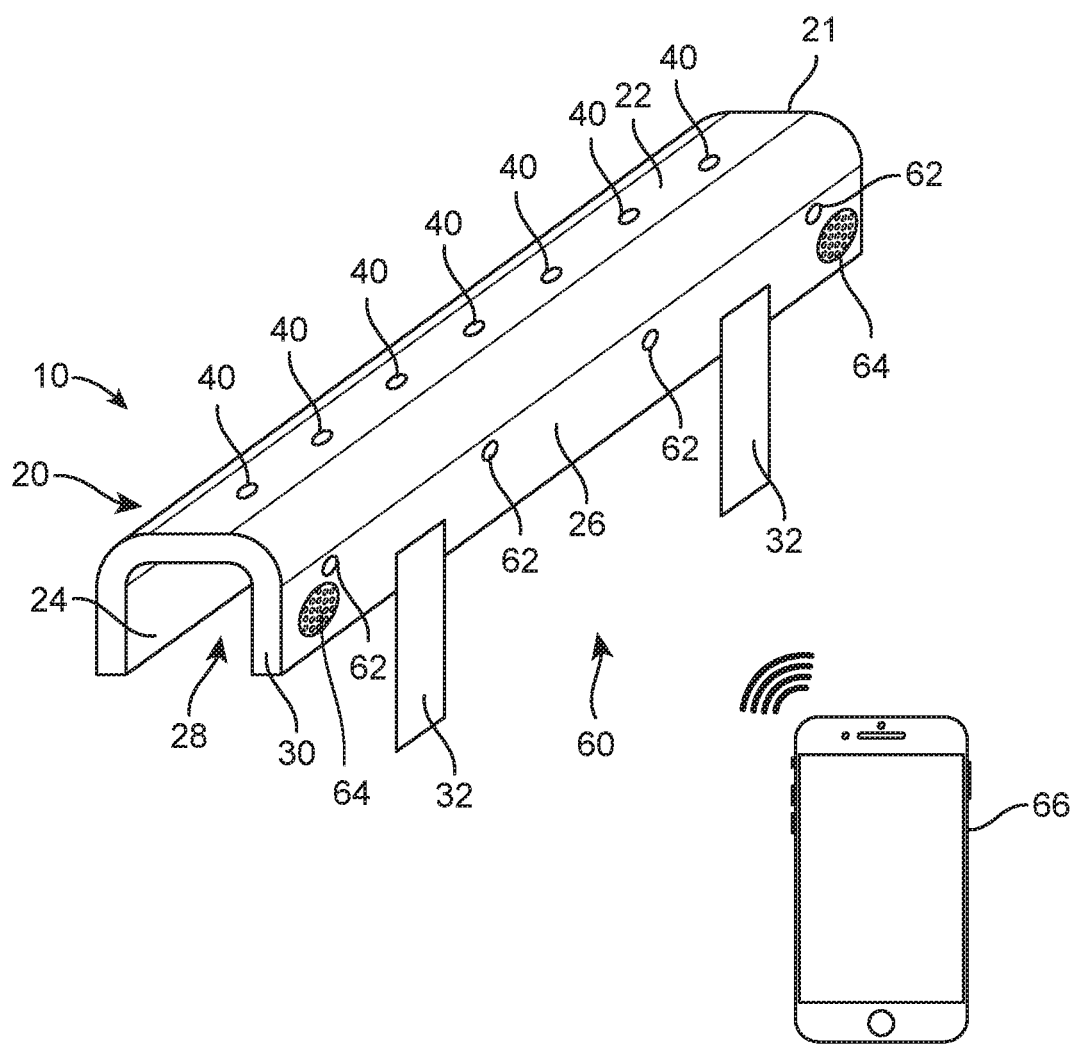
FIG. 1 represents an isometric view of the present invention.

Referring now to the drawings, where the present invention is generally referred to with numeral 10, it can be observed that it, an alert system for rails 10, basically includes a cover assembly 20, sensors 40 and an alert assembly 60.

There is often a need for parents, guardians or caretakers to momentarily leave a child unattended to accomplish other household tasks and chores. It may not be possible to monitor a child entirely around the clock, for example, while a child sleeps it is not ideal to watch the child sleep in their crib. As such it is possible, that the child may unexpectedly awaken while there is no guardian present and the child may then attempt to climb over the rails of the crib. In that event, the child may possibly get seriously injured should they successfully climb over the rails and fall to the ground. Hence, there is a need to alert the guardian of a child climbing rails before the child can get seriously injured.

Figure 2:
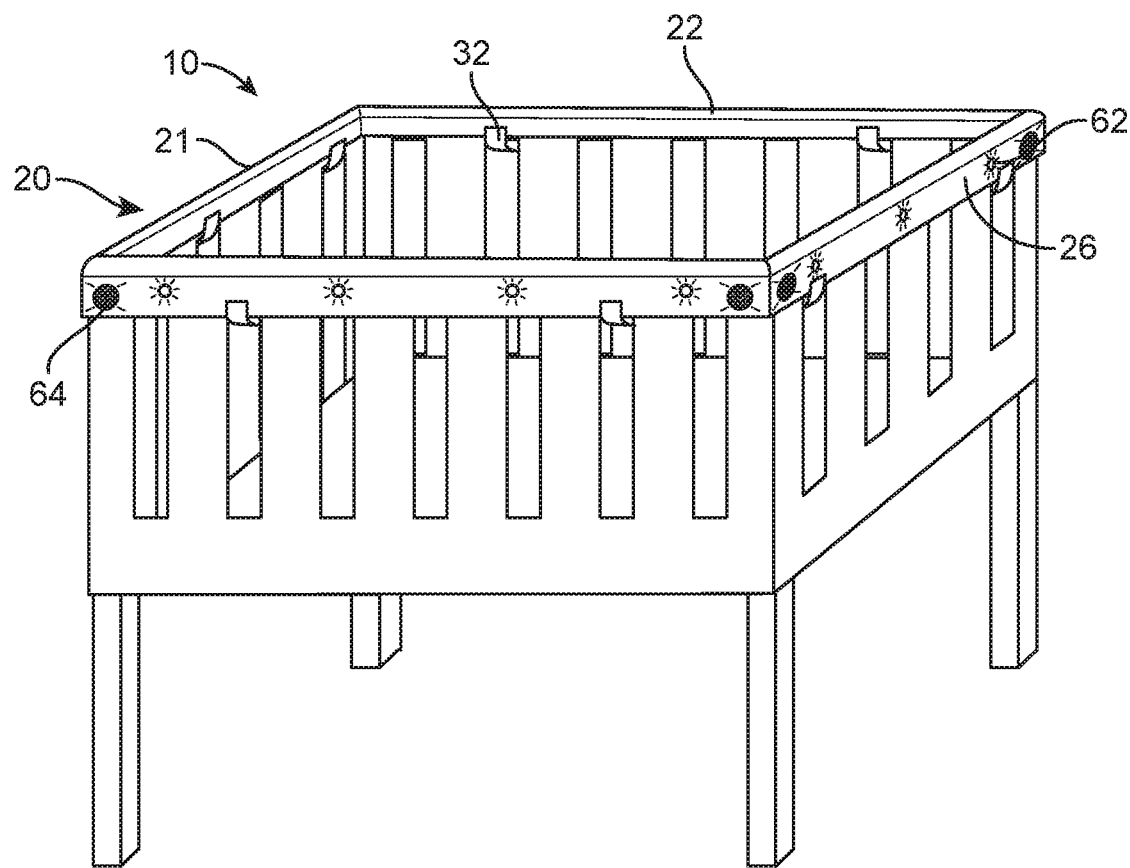
FIG. 2 shows the present invention mounted to a rail such as a crib rail.
Figure 3:
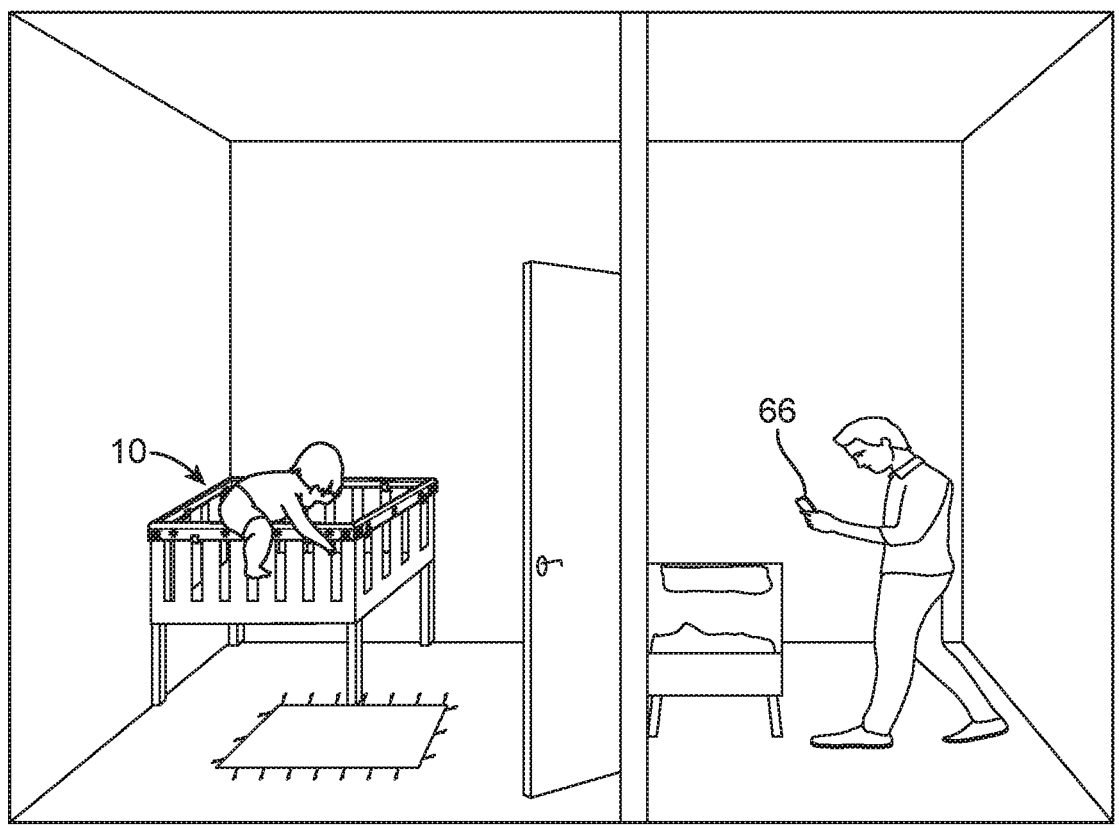
FIG. 3 illustrates the present invention in an operational setting. The operational setting being the present invention mounted onto a rail such as a crib rail with a child attempting to climb over the rail and a guardian being alerted of such an event.

In can be seen in FIG. 1-3, that alert system for rails 10 is shown. Importantly, the present invention includes cover assembly 20 having a body 21. It can be seen that cover assembly 20 may preferably be U-shaped in order to be mounted atop rails of any sort, such as crib rails or gate rails, for example. It can be seen that body 21 includes a top portion 22, a first side 24 and a second side 26. Top portion 22 may have a significant length that extends across and on top of rails. First side 24 and second side 26 may be entirely underneath top portion 22 and may be seen extending downward from top portion 22. First side 24 and second side 26 may extend downward from the longer peripheral edges of top portion 22. First side 24 and second side 26 may extend the same length as top portion 22. First side 24 and second side 26 may preferably extend to the sides of a rail, thereby meaning that the rail may be sandwiched in between first side 24 and second side 26 in an opening 28 of cover assembly 20, as can be seen in FIG. 2. Altogether, top portion 22, first side 24 and second side 26 comprise body 21 of cover assembly 20. Body 21 may preferably be in a shape that cooperates with being mounted onto a railing, hence why a U-shaped configuration with opening 28 may be preferred. It should be understood that body 21 is not limited to be that shape, any other shape that cooperates with being mounted onto rails may be suitable. Cover assembly 20 and body 21 may be made of virtually any material, such as rubber, plastic, cotton and the like. It may be preferred that body 21 of cover assembly be made of a material capable of providing some sort of cushioning. Hence, body 21 also includes thickness 30 to provide that cushioning between a person and railings. This helps to further increase the safety of a child. Cover assembly 20 may further include a plurality of straps 32 mounted to one of either first side 24 or second side 26 of body 21. Straps 32 may be mounted across the length of either first side 24 or second side 26. It may be suitable for straps 32 to be evenly spaced apart but otherwise may be suitable as well. Functionality of straps 32 is not hindered. Straps 32 may be mounted onto body 20 through an adhesive, sewing, buttons, fasteners, hook and loop straps, snap buttons or the like as known in the art of mounting. It may be suitable for straps 32 to be made of elastic, rubber, cotton or the like. Straps 32 may be used to secure the present invention to a railing. Straps 32 may extend underneath of railings. Preferably, straps 32 extend from one of either first side 24 or second side 26 across opening 28 and onto either first side 24 or second side 26. Meaning that if straps 32 are mounted onto first side 24 then straps 32 extend across opening 28 and onto second side 26 or vice versa. Straps 32 may be secured on the opposite side, either first side 24 or second side 26, through an adhesive, sewing, buttons, fasteners, hook and loop straps, snap buttons or the like as known in the art of mounting and securing. In FIG. 2, it can be seen how alert system for rails 10 mounts to a railing, a crib railing in this instance. The top, bottom, left and right rail are covered by cover assembly 20 as the present invention. It should be understood that the present invention and more importantly, that cover assembly 20, may be flexible enough to allow cover assembly 20 to be mounted about corners or curves of railings such as crib rail corners.

Importantly, integrated into body 21 of cover assembly 20 are a plurality of sensors 40. Preferably, sensors 40 are located along the length of top portion 22 of body 21. Sensors 40 may be weight sensors which detect weight being supported on body 21 of cover assembly 20, such as a child attempting to climb over the rails of a crib, for example. Sensors 40 may be configured to generate a signal once weight beyond a predefined threshold is surpassed. Sensors 40 may be connected to a microprocessor in order to send signals to alert assembly 60 once the weight limit threshold has been surpassed. The weight limit threshold being surpassed on sensors 40 indicates that a person, most often a child, is on cover assembly 20. That is a dangerous situation that is to be prevented as much as possible with the present invention. It is essential for communication to occur between sensors 40 and alert assembly 60. It may be possible for the communication between sensors 40 and alert assembly 60 to occur by means other than a microprocessor. Sensor 40 and alert assembly 60 may be directly connected with one another through electrical means such as by a wire. Alert assembly 60 may further include lights 62, a speaker 64 and a mobile device 66. Sensors 40 are configured to generate a signal that may be sent to alert assembly 60 to activate an alert when the predefined weight threshold has been surpassed. Upon such a case, alert assembly 60 activates one of lights 62, speaker 64, mobile device 66 or combinations thereof. Lights 62 may be used to generate a flashing light alert of any predetermined color to bring attention to a guardian of a child that a dangerous situation has arisen. Lights 62 may flash or they may be steady and bright. The light alert of lights 62 may be beneficial if the child climbing the railing is in sight. Speakers 64 may be used to generate an audible alert or alarm if sensors 40 detect that the weight threshold has been surpassed. Thereby allowing a guardian of a child to be aware of a dangerous situation without necessarily being in the direct vicinity of the child attempting to climb over rails. Further, another alert that may be generated by alert assembly 60 may be to mobile device 66. Mobile device 66 may be alerted in the form of a text message, a phone call, a notification, a vibration, an audible sound or combinations thereof. Thereby allowing a guardian to be aware of a child attempting to climb over a rail even when they are not near the child. Lights 62 may be mounted onto body 21 of cover assembly 20 nearly anywhere so long as they are visible. Preferably, lights 62 are mounted on the exterior side of one of first side 24 or second side 26. In an alternative embodiment, lights 62 may be mounted to both first side 24 and second side 26. Speakers 64 may be mounted onto body 21 of cover assembly 20 nearly anywhere. Preferably, speakers 64 are mounted on the exterior side of one of first side 24 or second side 26. In an alternative embodiment, speakers 64 may be mounted to both first side 24 and second side 26. In an alternate embodiment, just one of speakers 64 may be mounted onto body 21 of cover assembly 20. The more of speakers 64 used the louder and more audible the alert generated may be. The alerts may occur through one of lights 62, speakers 64 or mobile device 66. Alternatively, alerts may occur through lights 62, speakers 64 or mobile device 66 all at the same time or simultaneously.

It may be necessary to increase the safety of a child that is meant to be secured in place by railings of either a crib, bed or gate, for example. However, at times the child might be momentarily left unattended and they may attempt to climb over the railings at that time. This is a dangerous situation that can lead to serious injury and as such it is preferred to be avoided. Hence, the present invention achieves this increase in safety by alerting a guardian, care taker, parent etc., that a dangerous situation has presented itself. Thereby allow the guardian to handle the situation before injury occurs. The guardian may not even need to be in the vicinity of the child when they are alerted which may give them more peace of mind.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An alert system for rails, comprising:
a. a cover assembly having a body, said body including a top portion, a first side and a second side, said first side and said second side extending downwardly from longer peripheral edges of said top portion of said body, said body having a U-shaped configuration, said body further including an opening therebetween said first side and said second side adapted to receive railings;
b. straps mounted on one of either said first side or said second side;
c. sensors integrated into the top portion of said body;
d. an alert assembly; and
e. said railings covered and protected by said cover assembly.

2. The system of claim 1 wherein said sensors are weight sensors adapted to detect a weight beyond a predetermined threshold thereon.

3. The system of claim 1, wherein said body includes a thickness adapted to provide cushioning.

4. The system of claim 1, wherein said straps secure to both of said first side and said second side when securing said cover assembly to said rail.

5. The system of claim 1, wherein alert assembly further includes lights, adapted to activate upon said sensors detecting a predetermined threshold being surpassed, said lights flash.

6. The system of claim 5, wherein said alert assembly further includes speakers adapted to activate upon said sensors detecting a predetermined threshold being surpassed, said speakers generate an audible alarm.

7. The system of claim 6, wherein said alert assembly further includes a mobile device adapted to generate an alert in the form of a text message, a phone call, a notification, a vibration, an audible sound or combinations thereof.

8. The system of claim 7, wherein said alert from said lights, said speakers and said mobile device occur simultaneously.

9. The system of claim 1, wherein said cover assembly entirely covers said railings.

10. The system of claim 1, wherein said cover assembly is flexible enough to be mounted about corners or curves of said railings.

* * * * *